United States Patent [19]

Sipio

[11] Patent Number: 4,624,964
[45] Date of Patent: Nov. 25, 1986

[54] ARYL OXO-ALKYNOATES AS 5-LIPOXYGENASE INHIBITORS

[75] Inventor: William J. Sipio, Lindenwold, N.J.

[73] Assignee: E. I. Du Pont de Nemours and Company, Wilmington, Del.

[21] Appl. No.: 716,480

[22] Filed: Mar. 27, 1985

[51] Int. Cl.$^4$ .................... A61K 31/24; C07C 69/738
[52] U.S. Cl. .................... 514/539; 514/545; 560/47; 560/48; 560/51; 560/53
[58] Field of Search .................... 560/45, 47, 48, 51, 560/53; 514/539, 545; 562/457, 459, 463

[56] References Cited

U.S. PATENT DOCUMENTS

| | | | |
|---|---|---|---|
| 3,409,424 | 11/1968 | Brewbaker | 560/53 |
| 3,592,922 | 7/1971 | Gier et al. | 424/331 |
| 3,812,262 | 5/1974 | Chodnekar et al. | 424/282 |
| 3,839,455 | 10/1974 | Scherm et al. | 260/592 |
| 4,405,810 | 9/1983 | Blythin et al. | 562/495 |

FOREIGN PATENT DOCUMENTS

| | | |
|---|---|---|
| 101023 | 2/1984 | European Pat. Off. |
| 57072921 | 10/1980 | Japan |
| 56-1544402 | 11/1981 | Japan .................... 514/545 |

OTHER PUBLICATIONS

Herrmann et al., *J. Am. Chem. Soc.*, vol. 101, No. 6, pp. 1544–1549, (1979).
Kulkarni et al., *Chemical Abstracts*, vol. 70, No. 96356q, (1969).
Sakurai et al., Chemical Abstracts, vol. 69, No. 94792j, (1969).
Chan et al., *J. Org. Chem.* vol. 43, No. 18, pp. 3435–3440, (9/1/78).
Pirkle et al. *J. Org. Chem.*, vol. 43, No. 11, pp. 2091–2093, (5/26/78).
T. Fukumaru et al. in *Agr. Biol. Chem.*, 39, 519 (1975).
M. M. Midland et al. in *J. Am. Chem. Soc.*, 102, 867 (1980).
H. Dürr et al. in *Justus Liebigs Ann Chem.*, 7, 1140 (1974).
H. Saikachi et al., *Chem. Pharm. Bull.*, 27, 2857 (1979).
J. Bastide et al., *Tetrahedron Lett.*, 41, 4225 (1972).
Harland et al., Chemical Abstract, vol. 99, No. 105072x, (1983).

Primary Examiner—Natalie Trousof
Assistant Examiner—Bruce D. Gray

[57] ABSTRACT

Aryl oxo-alkynoates are 5-lipoxygenase inhibitors, making them useful for the treatment of inflammation, chronic obstructive lung disease or psoriasis. These compounds have the formula:

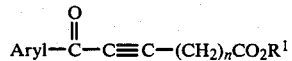

wherein
n is 1–12;
$R^1$ is $C_1$–$C_6$ alkyl, $C_2$–$C_6$ alkenyl, or phenyl; and
Aryl is naphthyl, phenyl or phenyl substituted with a variety of groups.

36 Claims, No Drawings

ARYL OXO-ALKYNOATES AS 5-LIPOXYGENASE INHIBITORS

BACKGROUND OF THE INVENTION

1. Field of Invention

This invention relates to aryl oxo-alkynoates, intermediates and processes for their preparation, pharmaceutical compositions containing them and pharmaceutical methods using them.

2. Prior Art

U.S. Pat. No. 4,405,810 issued Sept. 20, 1983 to Blythin et al. discloses 7-arylhept-5-ynoic acids and derivatives thereof as anti-allergy and antiinflammatory agents. These compounds have the formula:

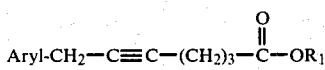

where
$R_1$ is H, lower alkyl or phenyl, and
Aryl is naphthyl or

where R includes H, phenyl, alkyl, phenoxy, and phenyl $(CH_2)_m$ where m is 0–2.

U.S. Pat. No. 3,839,455 issued Oct. 1, 1974 to Scherm and Peteri discloses 1-alkenyl-2-benzoyl-acetylenes of the formula

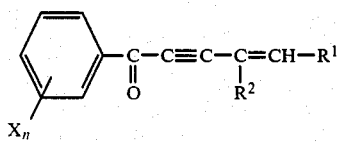

wherein $R^1$ and $R^2$ can be alike or different and can be hydrogen or lower alkyl containing 1 to 6 carbon atoms; X is halo and n=0–5, preferably 0–2. These compounds are disclosed as having fungistatic and bacteriostatic activity.

U.S. Pat. No. 3,592,922 issued July 13, 1971 to Gier and Calhoon discloses acetylenic ketones of the formula

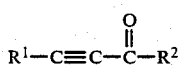

wherein $R^1$ is ethyl or phenyl and $R^2$ is lower alkyl, phenyl, alkylphenyl, phenylethenyl, benzyl, halophenyl, alkenyl or halophenoxymethyl. The compounds are disclosed as plant fungicides and nematocides.

U.S. Pat. No. 3,812,262 issued to Chodnekar et al. on May 21, 1974 discloses substituted propiolophenones of the formula

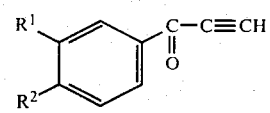

where $R^1$ and $R^2$ are hydrogen, hydroxy, halogen, lower alkyl, lower alkoxy or propynyloxy or together represent a lower alkylenedioxy group with the condition that both are not hydrogen. These compounds are disclosed as plant fungicides, nematocides, and insecticides.

T. Fukumaru et al. in *Agr. Biol. Chem.*, 39, 519(1975) disclose acetylenic ketone compounds having antiinflammatory and antimicrobial activity.

M. M. Midland et al. in *J. Am. Chem. Soc.*, 102, 867 (1980) describe the reduction of $\alpha,\beta$-acetylenic ketones. No biological activity for these compounds is disclosed.

H. Dürr et al. in *Justus Liebigs Ann Chem.*, 7, 1140 (1974) describe the formation of N-heterocycles by the 1,3 dipolar cycloaddition of a diazofluorene with alkynes of the formula

where $R^4$ is Me, COMe, COPh or $CO_2Me$ and $R^5$ is $NEt_2$, CHMeOH, COMe, COPh or $CO_2Me$. No biological activity for these alkynes is disclosed.

Acetylenic ketones are also disclosed as substrates in chemical reactions by H. Saikach et al., *Chem. Pharm. Bull.*, 27, 2857 (1979) and J. Bastide et al., *Tetrahedron Lett.*, 41, 4225 (1972).

Acetylenic ketones, useful for the production of heterocyclic compounds used as intermediates for the production of pharmaceuticals and agrochemicals are disclosed in Japanese Patent 5707291 issued May 7, 1982.

Co-assigned U.S. patent application Ser. No. 650,187 filed on Sept. 13, 1984 discloses aryl alkynes as 5-lipoxygenase inhibitors, of the general formula

SUMMARY OF INVENTION

According to the present invention, there is provided a compound of Formula (I)

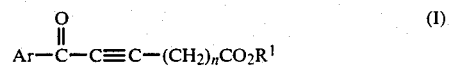

wherein
$R^1$ is $C_1$–$C_6$ alkyl, $C_2$–$C_6$ alkenyl, or phenyl;
n is 1–12 with the proviso that when n is 6–12 then $R^1$ is $C_1$–$C_3$ alkyl;
Ar is naphthyl or

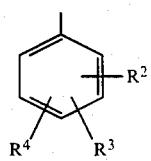

provided that at least one ortho position is hydrogen;

$R^2$, $R^3$ and $R^4$ independently are H, halogen, $CF_3$, $C_1$-$C_{12}$ alkyl, $C_2$-$C_{12}$ alkenyl, $C_1$-$C_6$ alkoxy or

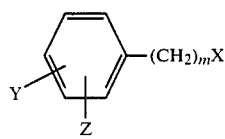

where
m is 0-6;
Y and Z independently are H, Cl, $C_1$-$C_3$ alkyl, or $C_1$-$C_3$ alkoxy; and
X is O, N-phenyl, or $CH_2$;
or a pharmaceutically suitable salt thereof.

Also provided are pharmaceutical compositions containing a lipoxygenase inhibiting amount of a compound of Formula (I) and a suitable pharmaceutical carrier.

Further provided are methods of treating inflammation, chronic obstructive lung disease or psoriasis in a mammal which comprise administering to the mammal an effective amount of a compound of Formula (I).

Additionally provided is a process for the preparation of Formula (I) compounds which comprise: reacting an aryl aldehyde, ArCHO, with an alkyne which has been pretreated with a strong base such as n-butyllithium, and oxidizing the resulting alcohol with pyridinium chlorochromate (PCC).

DETAILED DESCRIPTION OF THE INVENTION

Preferred for their lipoxygenase inhibitory activity are those compounds of Formula (I) where:
n is 1-6; or
$R^1$ is $C_1$-$C_3$ alkyl; or
Ar is

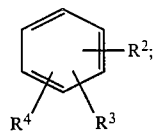

where $R^2$, $R^3$ and $R^4$ are as defined above and preferably $R^3$ and $R^4$ are H; and
$R^2$ is halogen, $C_1$-$C_6$ alkoxy, or

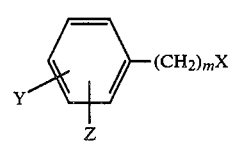

where m, X, Y and Z are as defined above.

More preferred compounds are those preferred compounds where:
n is 3-5; or
$R^1$ is $C_1$-$C_3$ alkyl; or
$R^2$ is

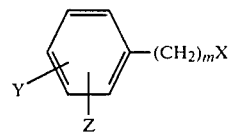

where
m is 0,
X is as defined above, and
Y and Z independently are H or Cl;
and $R^3$ and $R^4$ are H.

Specifically preferred for their lipoxygenase inhibitory activity are:
(a) Methyl 7-oxo-7-[2-(phenylmethyl)phenyl]-5-heptynoate
(b) Methyl 7-oxo-7-(2-phenoxyphenyl)-5-heptynoate
(c) Methyl 7-oxo-7-[2-(2,4-dichlorophenoxy)phenyl]-5-heptynoate
(d) Methyl 7-oxo-7-[2-(diphenylamino)phenyl]-5-heptynoate

SYNTHESIS

The compounds of Formula (I) can be prepared in a two step sequence as shown in Schemes (1) and (2). An aryl aldehyde of Formula (II), where Ar is as previously defined, is reacted with an appropriate alkyne (III) which has been pretreated with a strong base such as n-butyllithium (n-BuLi). The reactions are carried out under a nitrogen atmosphere in dry tetrahydrofuran between $-78°$ C. and room temperature.

Scheme (1)

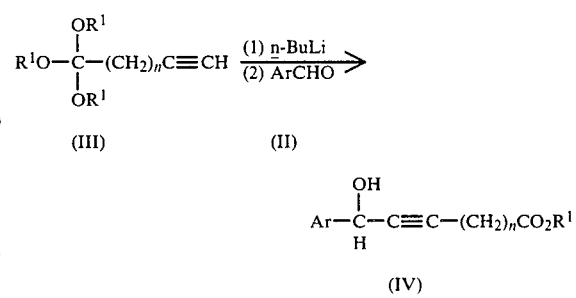

Aqueous workup provides alcohols of Formula (IV) in which Ar is as previously defined.

Aryl ketones of Formula (I) are prepared in a second step by oxidation of the alcohols of Formula (IV).

Scheme (2)

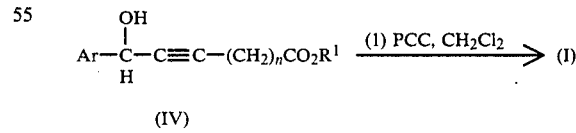

This reaction is carried out under a nitrogen atmosphere at room temperature in methylene chloride ($CH_2Cl_2$) with pyridinium chlorochromate (PCC). Alkynes of Formula (III) may be prepared according to the procedure described by G. Just and C. Luthe, *Tetrahedron Letters*, 23, 1331 (1982).

The compounds of the invention and their synthesis are further illustrated by the following example. All temperatures are in degrees Centrigrade and parts and percentages by weight.

EXAMPLE 1

(a) Methyl 7-hydroxy-7-[2-(phenylmethyl)phenyl]-5-heptynoate

To a stirred mixture of 2.19 g (12.73 mmol) 1,1,1-trimethoxy-5-hexyne in 15 ml dry tetrahydrofuran (THF) at −78° under nitrogen was added 8.37 ml of 1.52M n-butyllithium (12.73 mmol) in hexane dropwise. The mixture was stirred at −78° for 1 hour and 2.0 g of 2-benzylbenzaldehyde (10.20 mmol) in 10 ml dry THF was added dropwise at −78°. The mixture was stirred at room temperature for 12 hours and poured into water. The reaction mixture was extracted with ether (2×75 ml) and the combined organic layers were washed with water (50 ml), saturated sodium chloride (50 ml), and dried (MgSO$_4$). Filtration and evaporation left an oil that was purified by flash chromatography to give the title compound in 56% yield (2.02 g). NMR (CDCl$_3$, 200 MHz) δ: 1.80 (m, 2H), 2.25–2.50 (m, 5H), 3.67 (s, 3H), 4.18 (br s, 2H), 5.60 (s, 1H), 7.12–7.75 (m, 9H). Mass spectrum: m/z=322 (M+).

(b) Methyl 7-oxo-7-[2-(phenylmethyl)phenyl]-5-heptynoate

To a stirred mixture of 0.3 g (0.93 mmol) methyl 7-hydroxy-7-[2-(phenylmethyl)phenyl]-5-heptynoate in 20.0 ml methylene chloride at room temperature was added 0.5 g (2.32 mmol) of pyridinium chlorochromate (PCC). The mixture was stirred for 2 hours and 80.0 ml of diethylether was added to the reaction mixture. The reaction mixture was filtered through Florisil ® brand magnesium silicate evaporated to an oil and purified by flash chromatography to give the title compound in 67% yield (200 mg; 0.625 mmol). NMR (CDCl$_3$, 200 MHz) δ: 2.0 (m, 2H), 2.5 (m, 4H), 3.67 (s, 3H), 4.40 (s, 2H), 7.12–8.25 (m, 9H). Mass spectrum: m/z=320 (M+).

The compound of Example 1 and compounds which were prepared following procedures analogous to those outlined above are shown in Table 1.

TABLE 1

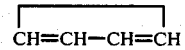

| Example | R$^2$ | R$^3$ | R$^4$ | Mass Spectrum (m/z) |
|---|---|---|---|---|
| 1 | CH$_2$C$_6$H$_5$ | H | H | 320 |
| 2 | Br | H | H | 308 |
| 3 | H | Br | H | 308 |
| 4 | H | H | Br | 308 |
| 5 | OCH$_3$ | H | H | 260 |
| 6 | H | OCH$_3$ | H | 260 |
| 7 | H | H | OCH$_3$ | 260 |
| 8 | F | H | H | 248 |
| 9 | H | F | H | 248 |
| 10 | H | H | F | 248 |
| 11 | Cl | H | H | 264 |
| 12 | H | Cl | H | 264 |
| 13 | H | H | Cl | 264 |
| 14 | H | H | H | 230 |
| 15 | H | H | CF$_3$ | 298 |
| 16 | H | Cl | Cl | 298 |
| 17 | CH$_3$ | H | H | 244 |
| 18 | H | CH$_3$ | H | 244 |

TABLE 1-continued

| Example | R$^2$ | R$^3$ | R$^4$ | Mass Spectrum (m/z) |
|---|---|---|---|---|
| 19 | H | H | CH$_3$ | 244 |
| 20 | H | H | OCH$_2$C$_6$H$_5$ | 336 |
| 21 | OC$_6$H$_5$ | H | H | 322 |
| 22 | 2,4-Cl$_2$C$_6$H$_3$O | H | H | 390 |
| 23 | N(C$_6$H$_5$)$_2$ | H | H | 397 |
| 24 | H | CH=CH—CH=CH | | 280 |

DOSAGE FORMS

The lipoxygenase inhibitors of this invention can be administered to treat inflammation, allergy, chronic obstructive lung diseases such as asthma and bronchitis, or psoriasis by any means that produces contact of the active agent with the inhibitor's site of action in the body of a mammal. They can be administered by any conventional means available for use in conjunction with pharmaceuticals, either as individual therapeutic agents or in a combination of therapeutic agents. They can be administered alone, but are generally administered with a pharmaceutical carrier selected on the basis of the chosen route of administration and standard pharmaceutical practice.

The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Usually a daily dosage of active ingredient can be about 0.1 to 100 milligrams per kilogram of body weight. Ordinarily 0.5 to 50, and preferably 1 to 10 milligrams per kilogram per day given in divided doses 1 to 6 times a day or in sustained release form is effective to obtain desired results.

Dosage forms (compositions) suitable for internal administration contain from about 1 milligram to about 500 milligrams of active ingredient per unit. In these pharmaceutical compositions the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions. It can also be administered parenterally, in sterile liquid dosage forms, by inhalation in the form of a nasal spray or lung inhaler, or topically as an ointment, cream or lotion.

Gelatin capsules contain the active ingredient and powdered carriers, such as lactose, sucrose mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain the active ingredient, suitable stabilizing agents, and if necessary, buffer substances. Antioxidizing agents such as sodium bisulfite, sodium sulfite, or ascorbic acid either alone or combined are suitable stabilizing agents. Also used are citric acid and its salts and sodium EDTA. In addition, parenteral solutions can contain preservatives, such as benzalkonium chloride, methyl or propyl-paraben, and chlorobutanol.

Suitable pharmaceutical carriers are described in *Remington's pharmaceutical Sciences*, A. Osol, a standard reference text in this field.

Useful pharmaceutical dosage forms for administration of the compounds of this invention can be illustrated as follows:

Capsules

A large number of unit capsules are prepared by filling standard two-piece hard gelatin capsules each with 50 milligrams of powdered active ingredient, 175 milligrams of lactose, 24 milligrams of talc, and 6 milligrams of magnesium stearate.

Soft Gelatin Capsules

A mixture of active ingredient in soybean oil is prepared and injected by means of a positive displacement pump into gelatin to form soft gelatin capsules containing 50 milligrams of the active ingredient. The capsules are washed in petroleum ether and dried.

Tablets

A large number of tablets are prepared by conventional procedures so that the dosage unit is 50 milligrams of active ingredient, 6 milligrams of magnesium stearate, 70 milligrams of microcrystalline cellulose, 11 milligrams of cornstarch and 225 milligrams of lactose. Appropriate coatings may be applied to increase palatability or delay absorption.

Injectable

A parenteral composition suitable for administration by injection is prepared by stirring 1.5% by weight of active ingredient in 10% by volume propylene glycol and water. The solution is sterilized by commonly used techniques.

Suspension

An aqueous suspension is prepared for oral administration so that each 5 milliliters contain 25 milligrams of finely divided active ingredient, 200 milligrams of sodium carboxymethyl cellulose, 5 milligrams of sodium benzoate, 1.0 grams of sorbitol solution, U.S.P., and 0.025 milliliters of vanillin.

Nasal Spray

An aqueous solution is prepared such that each 1 milliliter contains 10 milligrams of active ingredient, 1.8 milligrams methylparaben, 0.2 milligrams propylparaben and 10 milligrams methylcellulose. The solution is dispersed into 1 milliliter vials.

Lung Inhaler

A homogeneous mixture of the active ingredient in polysorbate 80 is prepared such that the final concentration of the active ingredient will be 10 milligrams per container and the final concentration of polysorbate 80 in the container will be 1% by weight. The mixture is dispensed into each can, the valves are crimped onto the can and the required amount of dichlorotetrafluoroethane is added under pressure.

Topical Formulation

An ointment for topical administration may be prepared by adding the active ingredient to a mixture of 48% by weight white petrolatum, 10% liquid petrolatum, 8% glycerol monostearate, 3% isopropyl myristate and 20% lanolin at 70° C. After thorough mixing, a warm solution of methyl and propyl parabens in water containing sodium acetone bisulfite is added such that the final concentrations of each paraben is 0.15%, of water is 8% and of sodium acetone bisulfite is 0.5%. The mixture is stirred until it has reached room temperature.

Use

The compounds of this invention have been shown to inhibit 5-lipoxygenase in an in vitro test system using rat basophilic leukemia (RBL-1) cells as the source of enzyme. The test method is a modification of the procedures developed by Jackchik et al (Prostaglandins, 16, 733–748 (1978), Biochem. Biophys. Res. Comm., 95, 103–110 (1980), 102, 624–629 (1981). The 10,000 xg supernatant from homogenized RBL-1 cells was incubated with drug in a pH 7.0 phosphate buffer for five minutes. $^{14}$C-arachidonic acid was added to initiate the reaction which was allowed to continue at 37° C. for two minutes. The reaction was stopped by freezing in a dry ice/ethanol slurry, and the 5-lipoxygenase products were separated from the substrate on silica gel columns. The amount of individual lipoxygenase products produced was determined and the percent inhibition calculated.

The enzyme 5-lipoxygenase catalyzes the first reaction in the biosynthesis of the potent biological mediators, the leukotrienes (LTB$_4$, LTC$_4$, LTD$_4$, LTE$_4$) from arachidonic acid. Collectively LTC$_4$, LTD$_4$, and LTE$_4$ are the materials which used to be known as slow reacting substance of anaphylaxis (SRS-A) before they were chemically characterized as leukotrienes. LTC$_4$ and LTD$_4$ are extremely potent mediators of anaphylaxis and seem to be particularly effective at reducing the air flow in peripheral airways. In animal models, reduction of the synthesis of SRS-A leads to a reduction in the symptoms following an allergic challenge. LTB$_4$ is a potent leukocyte chemotactic factor and aggregating agent. Polymorphonuclear leukocytes (PMN) are particularly sensitive to activation by LTB$_4$. Reduction of the synthesis of LTB$_4$ by blocking 5-lipoxygenase should reduce the influx of PMN to an inflamed site-either an arthritic joint or a psoriatic lesion. Elevated levels of LTB$_4$ have been found in both the synovial fluid of rheumatoid patients and in the plaque area of psoriasis patients. Thus a 5-lipoxygenase inhibitor, by reducing the production of these potent biological mediators, is useful for the treatment of inflammation, chronic obstructive lung diseases such as asthma and bronchitis, and skin diseases such as psoriasis.

What is claimed is:

1. A compound having the formula:

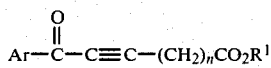 (I)

wherein
R$^1$ is C$_1$–C$_6$ alkyl, C$_2$–C$_6$ alkenyl, or phenyl;
n is 1–12 with the proviso that when n is 6–12 then R$^1$ is C$_1$–C$_3$ alkyl;
Ar is naphthyl or

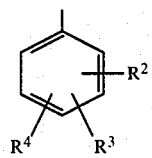

with the proviso that at least one ortho position is hydrogen;
R$^2$, R$^3$ and R$^4$ independently are H, halogen, CF$_3$, C$_1$–C$_{12}$ alkyl, C$_2$–C$_{12}$ alkenyl, C$_1$–C$_6$ alkoxy or

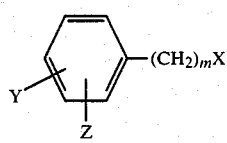

where
m is 0–6;
Y and Z independently are H, Cl, C$_1$–C$_3$ alkyl, or C$_1$–C$_3$ alkoxy; and
X is O, N-phenyl, or CH$_2$;
or a pharmaceutically suitable salt thereof.

2. A compound of claim 1 wherein n is 1–6.
3. A compound of claim 1 wherein R$^1$ is C$_1$–C$_3$ alkyl.
4. A compound of claim 1 wherein Ar is

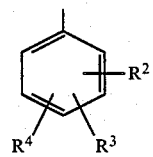

where R$^2$, R$^3$, and R$^4$ are as defined in claim 1.

5. A compound of claim 4 wherein R$^3$ and R$^4$ are hydrogen and R$^2$ is halogen, C$_1$–C$_6$ alkoxy, or

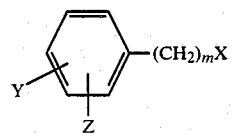

where m, X, Y and Z are as defined in claim 1.

6. A compound of claim 1 wherein
n is 1–6;
R$^1$ is C$_1$–C$_3$ alkyl; and
Ar is

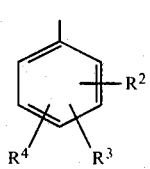

where
R$^3$ and R$^4$ are hydrogen and
R$^2$ is halogen, C$_1$–C$_6$ alkoxy, or

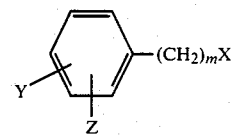

where
m, X, Y and Z are as defined in claim 1.

7. A compound of claim 6 wherein n is 3–5.
8. A compound of claim 7 wherein
m is 0;
X is as defined in claim 1; and
Y and Z independently are H or Cl.
9. The compound of claim 1 which is methyl 7-oxo-7-[2-(phenylmethyl)phenyl]-5-heptynoate.
10. The compound of claim 1 which is methyl 7-oxo-7-(2-phenoxyphenyl)-5-heptynoate.
11. The compound of claim 1 which is methyl 7-oxo-7-[2-(2,4-dichlorophenoxy)phenyl]-5-heptynoate.
12. The compound of claim 1 which is methyl 7-oxo-7-[2-(diphenylamino)phenyl]-5-heptynoate.
13. A pharmaceutical composition consisting essentially of a suitable pharmaceutical carrier and a lipoxygenase inhibiting amount of a compound of claim 1.
14. A pharmaceutical composition consisting essentially of a suitable pharmaceutical carrier and a lipoxygenase inhibiting amount of a compound of claim 2.
15. A pharmaceutical composition consisting essentially of a suitable pharmaceutical carrier and a lipoxygenase inhibiting amount of a compound of claim 3.
16. A pharmaceutical composition consisting essentially of a suitable pharmaceutical carrier and a lipoxygenase inhibiting amount of a compound of claim 4.
17. A pharmaceutical composition consisting essentially of a suitable pharmaceutical carrier and a lipoxygenase inhibiting amount of a compound of claim 5.
18. A pharmaceutical composition consisting essentially of a suitable pharmaceutical carrier and a lipoxygenase inhibiting amount of a compound of claim 6.
19. A pharmaceutical composition consisting essentially of a suitable pharmaceutical carrier and a lipoxygenase inhibiting amount of a compound of claim 7.
20. A pharmaceutical composition consisting essentially of a suitable pharmaceutical carrier and a lipoxygenase inhibiting amount of a compound of claim 8.
21. A pharmaceutical composition consisting essentially of a suitable pharmaceutical carrier and a lipoxygenase inhibiting amount of the compound of claim 9.
22. A pharmaceutical composition consisting essentially of a suitable pharmaceutical carrier and a lipoxygenase inhibiting amount of the compound of claim 10.
23. A pharmaceutical composition consisting essentially of a suitable pharmaceutical carrier and a lipoxygenase inhibiting amount of the compound of claim 11.

24. A pharmaceutical composition consisting essentially of a suitable pharmaceutical carrier and a lipoxygenase inhibiting amount of the compound of claim 12.

25. A method of treating inflammation, chronic obstructive lung disease or psoriasis in a mammal which comprises administering to the mammal an effective amount of a compound of claim 1.

26. A method of treating inflammation, chronic obstructive lung disease or psoriasis in a mammal which comprises administering to the mammal an effective amount of a compound of claim 2.

27. A method of treating inflammation, chronic obstructive lung disease or psoriasis in a mammal which comprises administering to the mammal an effective amount of a compound of claim 3.

28. A method of treating inflammation, chronic obstructive lung disease or psoriasis in a mammal which comprises administering to the mammal an effective amount of a compound of claim 4.

29. A method of treating inflammation, chronic obstructive lung disease or psoriasis in a mammal which comprises administering to the mammal an effective amount of a compound of claim 5.

30. A method of treating inflammation, chronic obstructive lung disease or psoriasis in a mammal which comprises administering to the mammal an effective amount of a compound of claim 6.

31. A method of treating inflammation, chronic obstructive lung disease or psoriasis in a mammal which comprises administering to the mammal an effective amount of a compound of claim 7.

32. A method of treating inflammation, chronic obstructive lung disease or psoriasis in a mammal which comprises administering to the mammal an effective amount of a compound of claim 8.

33. A method of treating inflammation, chronic obstructive lung disease or psoriasis in a mammal which comprises administering to the mammal an effective amount of the compound of claim 9.

34. A method of treating inflammation, chronic obstructive lung disease or psoriasis in a mammal which comprises adminstering to the mammal an effective amount of the compound of claim 10.

35. A method of treating inflammation, chronic obstructive lung disease or psoriasis in a mammal which comprises administering to the mammal an effective amount of the compound of claim 11.

36. A method of treating inflammation, chronic obstructive lung disease or psoriasis in a mammal which comprises administering to the mammal an effective amount of the compound of claim 12.

* * * * *